United States Patent [19]

Kawazi

[11] Patent Number: 4,963,361
[45] Date of Patent: Oct. 16, 1990

[54] ETOFENAMATE-CONTAINING ADHESIVE TAPE

[75] Inventor: Toshikuni Kawazi, Kagawa, Japan

[73] Assignee: Teikoku Seiyaku Kabushiki Kaisha, Kagawa, Japan

[21] Appl. No.: 177,043

[22] Filed: Apr. 4, 1988

[30] Foreign Application Priority Data

Apr. 2, 1987 [JP] Japan .................................. 62-82057

[51] Int. Cl.$^5$ .............................................. A61F 13/00
[52] U.S. Cl. .................................. 424/443; 424/447; 424/448
[58] Field of Search ................. 424/435, 447, 448, 449

[56] References Cited

U.S. PATENT DOCUMENTS

| | | | |
|---|---|---|---|
| 4,314,557 | 2/1982 | Chandrasekaran | 424/449 |
| 4,455,546 | 6/1984 | Noda et al. | 424/447 |
| 4,623,346 | 11/1986 | von Bittera et al. | 424/448 |
| 4,627,852 | 12/1985 | von Bittera et al. | 424/449 |
| 4,661,104 | 4/1987 | von Bittera et al. | 424/78 |
| 4,731,384 | 3/1988 | Dell et al. | 514/658 |
| 4,738,670 | 4/1988 | von Bittera | 604/302 |

Primary Examiner—Merrell C. Cashion, Jr.
Assistant Examiner—Leon R. Horne
Attorney, Agent, or Firm—Oblon, Spivak, McClelland, Maier & Neustadt

[57] ABSTRACT

An adhesive tape usable as an analgesic and antiinflammatory agent comprises a support member and an adhesive mass spread on the support member, which mass contains, as essential components, etofenamate as the active ingredient, a styrene-isoprene-styrene block copolymer as an adhesive ingredient, a tackifier resin, liquid paraffin as a softening agent, a liquid rubber as a softening agent and further an antioxidant.

7 Claims, 2 Drawing Sheets

ETOFENAMATE-CONTAINING ADHESIVE TAPE

BACKGROUND OF THE INVENTION

This invention relates to an etofenamate-containing adhesive tape.

Etofenamate has analgesic and antiinflammatory activities and therefore is used as a therapeutic agent for osteoarthritis, shoulder-arm-neck syndrome, arthritis, myalgia, swelling, pain and the like diseases. It has the structural formula:

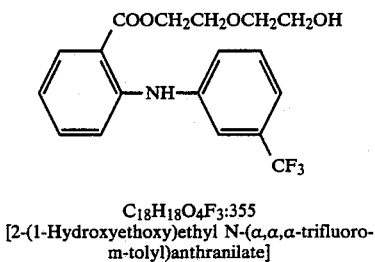

$C_{18}H_{18}O_4F_3:355$
[2-(1-Hydroxyethoxy)ethyl N-($\alpha,\alpha,\alpha$-trifluoro-m-tolyl)anthranilate]

So far, this therapeutic agent has been used generally in the form of oral preparations, suppositories or ointments. However, these dosage forms have the following problems:

[a] In the case of oral preparations and ointments:

(1) The drug (etofenamate) is absorbed through the intestinal tract into the blood circulation and then delivered to the affected site. The drug is thus distributed systemically. As a result, the drug concentration at the affected site becomes low and, in other words, the drug is utilized only incompletely and fails to produce its pharmacological effects to a desired extent.

(2) For promoting the pharmacological effects, it is necessary to administer the drug in a dose which is excessive to a certain extent so that an increased drug concentration can be attained at the affected site. However, excessive doses may possibly induce marked adverse effects on other sites than the affected site, in particular disorders in the stomach, liver, kidney, etc.

(3) In cases where the drug is absorbed through the intestinal tract, the drug absorption may vary widely depending on the food intake.

[b] In the case of ointments:

(1) The drug is absorbed through the skin. In that case, however, the drug absorption is in general incomplete. Furthermore, ointments are administered locally, so that it is difficult to produce the pharmacological effects of the drug intensively.

(2) Since it is not easy to apply ointments in a constant dose, the dose of the drug tends to vary.

(3) Since the drug absorption decreases with time, it is necessary to repeat application a number of times a day.

(4) For preventing clothing from contamination with ointments, covering with cloth, bandage or tape is required after application of ointments. Accordingly, the method of use is not simple. Furthermore, the use of a tape may cause dermatopathy.

OBJECT OF THE INVENTION

Accordingly, it is an object of the invention to provide an etofenamate-containing adhesive tape which can be easily applied to the affected site without requiring any troublesome procedure and is excellent in adherence to the skin and in removability from the skin and with which good percutaneous absorption, hence pharmacological effect, can be attained for a prolonged period of time.

SUMMARY OF THE INVENTION

The present invention thus provides an etofenamate-containing adhesive tape which comprises a support member and an adhesive mass essentially containing etofenamate, a styrene-isoprene-styrene block copolymer, a tackifier resin, liquid paraffin, a liquid rubber and an antioxidant, with said adhesive mass being spread on said support member.

The invention also provides a method of producing the above-mentioned adhesive tape which comprises spreading the adhesive mass mentioned above on a support member.

BRIEF DESCRIPTION OF THE DRAWINGS

In the accompanying drawings.

DETAILED DESCRIPTION OF THE INVENTION

Figure 1:
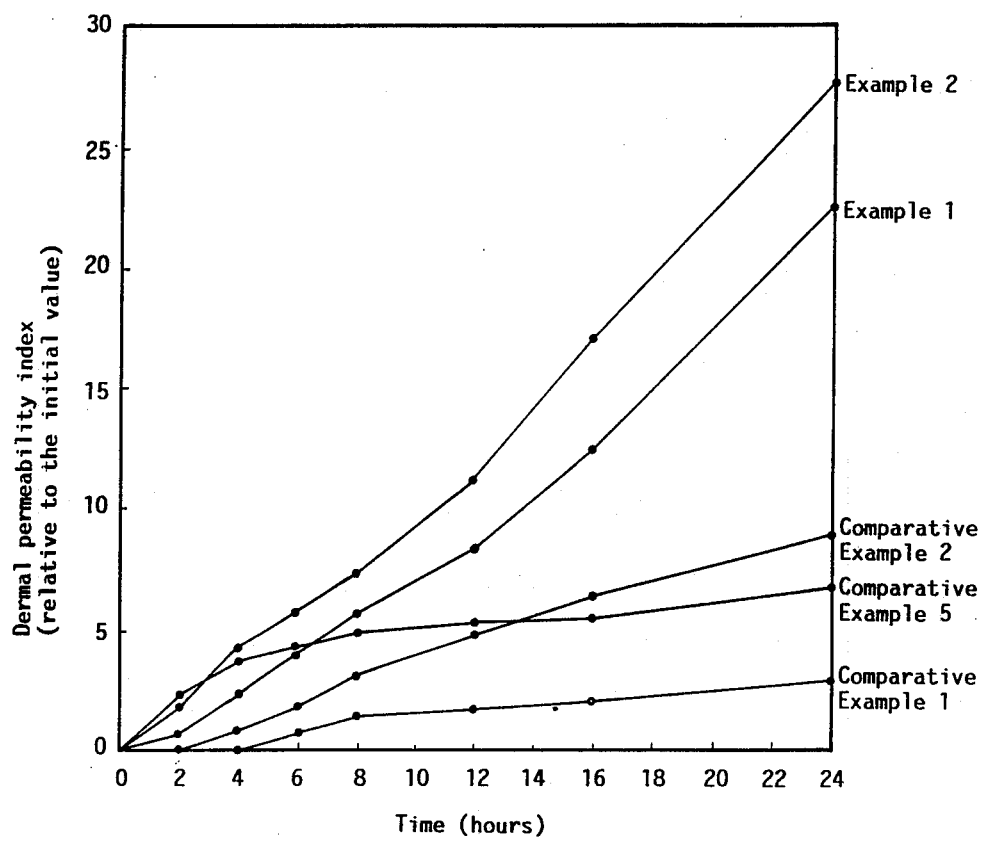
FIG. 1 shows the relationship between the time of contact of the adhesive tape or ointment with the skin and the dermal permeability index relative to the initial value for each of the adhesive tape samples prepared in accordance with the invention and the samples prepared in some comparative examples.

As mentioned above, the present invention is characterized in that etofenamate is contained in an adhesive mass comprising the above-specified particular components. The constituents of the adhesive mass are described below.

Styrene-isoprene-styrene block copolymer:

This block copolymer is capable of including the active ingredient therein and therefore the use thereof as an adhesive mass component assures stabilized release of etofenamate and prolonged production of the drug efficacy. When said block copolymer is appropriately combined with the other components, excellent rubber elasticity, cohesion and adhesion can be obtained. There is no particular limitation on the molecular construction, molecular weight and other aspects of the styrene-isoprene-styrene block copolymer. Preferably, however, the styrene/rubber ratio should be about 14/86, the hardness about 38, and the 300% modulus about 7 kg.

The block copolymer is used in the adhesive mass preferably in an amount of 20–40% (percent by weight; hereinafter the same shall apply). In amounts less than 20%, the cohesive strength of the adhesive mass becomes small, so that the adhesive mass may partly remain on the skin after removal of the adhesive tape. In amounts exceeding 40%, the adhesive mass becomes stiff and, even when the formulation is adjusted with respect to other components, the tackiness to the skin may become insufficient.

Tackifier resin:

The tackifier resin is added for the purpose of increasing the tackiness of the adhesive tape. No particular limitation is placed on the kind of tackifier resin. Preferred, however, are those resins which have good thermal stability and color stability and are as odorless as possible, for example alicyclic saturated hydrocarbon petroleum resins and hydrogenated rosin [commercially available under the trademarks Clearon (Yasuhara Yushi) and Arkon (Arakawa Chemical Industries), among others]. The tackifier resin is used preferably in an amount of 40-60%. At addition levels below 40%, the tackiness is insufficient, whereas, at levels over 60%, the viscosity becomes too great and makes it difficult to spread the adhesive mass on the support member.

Liquid paraffin and liquid rubber:

Liquid paraffin is used for the purpose of imparting softness to the adhesive mass. When liquid paraffin is used in combination with a liquid rubber, the initial adhesion to the skin and the resistance to slippage, for instance, can be adjusted, hence the adhesive tape can be prevented from slipping off the affected site. Liquid paraffin is compatible with the rubber component and shows softening action and at the same time has tackiness. It is used preferably at an addition level of 0.1-20%. At addition levels below 0.1%, the adhesive mass is not softtened to a sufficient extent, whereas, in amounts exceeding 20%, the adhesive mass is softened excessively and becomes incapable of holding the adhesive tape in place. The liquid rubber is used in an amount of 5-20%.

Antioxidant:

The styrene-isoprene-styrene block copolymer to be used as a main component of the adhesive mass contains a large number of double bonds remaining after 1,4-addition of isoprene. It is exposed to elevated temperatures in the process of adhesive tape manufacture. Therefore, for maintaining thermal stability and for stabilizing adhesive characteristics of adhesive tapes during storage, an antioxidant is added. The kind of antioxidant is not critical. Recommendable, however, are dibutylhydroxytoluene (BHT) and tetrakis(methylene-3,5-di-tert-butyl-4-hydroxyhydrocinnamate)methane (Irganox ® 1010; Ciba-Geigy) because they impart particularly good thermal stability to the adhesive mass. The antioxidant is used preferably at an addition level of 0.01-5%. At addition levels below 0.01%, the antioxidant effect is insufficient and, as a result, the adhesive mass is deficient in thermal stability and tackiness stability. Addition at levels exceeding 5% means waste of antioxidant action and is rather disadvantageous in that the contents of the remaining components are reduced. The upper limit is therefore set at 5%.

The active ingredient etofenamate occurs as an oil and can be readily incorporated in the adhesive mass. However, it can greatly influence the adhesive characteristics. Therefore, for rendering appropriate the coating amount of the adhesive mass and the etofenamate content and for increasing the bioavailability of the drug, the level of incorporation of etofenamate should preferably be in the range of 1-20%. In amounts less than 1%, the analgesic and antiinflammatory effects are unsatisfactory. On the other hand, when the level of incorporation exceeds 20%, the adhesive property of the adhesive mass may possibly be no longer retained. The thermal stability of etofenamate may be improved by addition of a sequestering agent.

The adhesive mass is spread over the supporting member generally at a coverage of 50-500 g/m$^2$, which is not limitative, however.

The support member to be used in the practice of the invention is desirably made of a flexible material allowing the adhesive tape to change its shape in agreement with the motion of the human body. Usable are various woven and nonwoven fabrics, flannel, laminates composed of a woven or nonwoven fabric or flannel and a polyethylene, ethylene-vinyl acetate copolymer or polyurethane film or the like, and, further, polyvinyl chloride films, polyethylene films, polyurethane films and other plastic films as well as composite films made of these films. For evaporation of the moisture resulting from sweating, the support member may be provided with perforations.

The following working examples and comparative examples are further illustrative of the present invention. It should be noted that the working examples are by no means limitative of the scope of the invention and that all the modifications readily conceivable to those skilled in the art with reference to the foregoing and the description which follows fall within the scope of the invention.

In the working examples and comparative examples, "part(s)" means "part(s) by weight" and each adhesive mass was applied to a release paper at a coverage of 100 g/m$^2$ after drying.

EXAMPLE 1

| | |
|---|---|
| Styrene-isoprene-styrene block copolymer (Cariflex ® TR-1107; Shell Chemical) | 25 parts |
| Tackifier resin (Arkon ® M-100; Arakawa Chemical Industries) | 50 parts |
| Liquid polyisoprene rubber (Kuraprene ® LIR-50; Kuraray Isoprene Chemicals) | 10 parts |
| Liquid paraffin | 3 parts |
| BHT | 2 parts |

The above ingredients were mixed and stirred for melting in a kneader heated at 150° C. to give an adhesive mass. This adhesive mass was cooled to 120° C., 10 parts of etofenamate was then added, and the whole mixture was malaxated with stirring. The adhesive mass thus obtained was applied to a release paper. After cooling, a nonwoven rayon fabric-ethylene-vinyl acetate copolymer film laminate (serving as a support member) was applied on the adhesive mass layer. The subsequent cutting to a desired size gave an adhesive tape according to the invention.

EXAMPLE 2

| | |
|---|---|
| Styrene-isoprene-styrene block copolymer (Cariflex ® TR-1107; Shell Chemical) | 30 parts |
| Tackifier resin (Clearon ® P105 | 45 parts |
| Liquid polybutene rubber (HV-300; Nippon Petrochemicals) | 10 parts |
| Liquid paraffin | 4.5 parts |
| Antioxidant (Irganox ® 1010; Ciba-Geigy) | 0.5 part |
| Etofenamate | 10 parts |

The above ingredients were used and the procedure of Example 1 was followed to give an adhesive tape according to the invention.

COMPARATIVE EXAMPLE 1

| | |
|---|---|
| Natural rubber | 40 parts and |
| Toluene | 250 parts | were mixed and stirred for dissolution of natural rubber, and

| | |
|---|---|
| Ester gum | 38 parts |
| Liquid polybutene rubber | 10 parts |

| BHT | 2 parts and |
| Etofenamate | 10 parts | were added to give a natural rubber-based adhesive mass with a solid content of 40%.

A release paper was coated with this adhesive mass, followed by drying and lamination to a plyurethane film. A sample was prepared by cutting to a desired size.

COMPARATIVE EXAMPLE 2

| 2-Ethylhexyl acrylate | 68 parts |
| Acrylic acid | 7 parts |
| Monomeric vinyl acetate | 25 parts |
| Azobisisobutyronitrile | 0.2 part |
| Ethyl acetate | 150 parts |

The above ingredients were placed in a four-necked flask under nitrogen. The mixture was heated at about 65° C. for 12 hours for effecting polymerization. To the thus-obtained acrylic adhesive mass (solid content 40%), there was added etofenamate in an amount of 10% relative to 90% of the solids. The resultant mixture was stirred and applied to a release paper, followed by drying and lamination to a polyurethane film. A sample was prepared by cutting to a desired size.

COMPARATIVE EXAMPLE 3

A sample was prepared by following the procedure of Example 1 and using the same formulation as used in Example 1 except that the use of BHT was omitted and the amount of liquid paraffin was increased by 2 parts instead.

COMPARATIVE EXAMPLE 4

A sample was prepared by following the procedure of Example 2 and using the same formulation as used in Example 2 except that the use of Irganox 1010 was omitted and, instead, the amount of liquid paraffin was increased by 0.5 part.

COMPARATIVE EXAMPLE 5

| White petrolatum | 40 parts |
| Cetanol | 20 parts |
| Sorbitan sesquioleate | 5 parts |
| Ethyl p-hydroxybenzoate | 0.1 part |
| Etofenamate | 10 parts |
| Purified water | 25 parts |

An ointment was prepared by treating the above ingredients by a conventional method.

TEST EXAMPLE 1

The adhesive tapes of Examples 1 and 2 and of Comparative Examples 1 and 2 and the ointment of Comparative Example 5 were tested for rat abdominal skin permeation of etofenamate using a Franz diffusion cell. Etofenamate was assayed by high-performance liquid chromatography (HPLC).

Except for the sample of Comparative Example 5 which was applied in the form of a circle, 2 cm in diameter, in the dose of 31.4 mg, a circular test piece, 2 cm in diameter, prepared from each adhesive tape sample by punching (each piece containing 3.14 mg of etofenamate) was applied to the rat skin, the resultant system was set on the cell and, after 2, 4, 8 12, 16 an 24 hours, the etofenamate penetration to the receptor side (phosphate buffer, pH 6.8) was determined.

The results obtained are shown in FIG. 1.

As is evident from the results shown in FIG. 1, continuous and better skin permeation of etofenamate was achieved with the samples according to the present invention over the 24-hour period of continued contact with the skin as compared with the samples of the comparative examples.

TEST EXAMPLE 2

Rats were used in groups of 10. After measurement of the right hind foot volume, 0.1 ml of 1% carrageenin suspension was injected into the pad of the same foot subcutaneously. Then, each test sample cut to the size 3.5 cm ×4.5 cm (etofenamate content 15.75 mg) (for Examples 1 and 2 and Comparative Examples 1 and 2) was applied. Four hours later, the sample was removed and the foot volume was again measured. The edema index was determined from the difference between the foot volume before application and that after 4 hours of application, and the percent inhibition relative to the control group was calculated for each sample. The sample of Comparative Example 5 was also tested in the same manner following application in the dose of 157.5 mg.

The results obtained are shown in Table 1.

TABLE 1

| Sample | Dose (mg) | Edema index (Mean ± S.D.) | Inhibition of edema (%) |
| --- | --- | --- | --- |
| Control | 15.75 | 86.5 ± 8.2 | — |
| Example 1 | " | 59.2 ± 9.2 | 31.6** |
| Example 2 | " | 58.7 ± 8.2 | 32.1** |
| Comparative Example 1 | " | 72.5 ± 11.4 | 16.2** |
| Comparative Example 2 | " | 65.4 ± 8.9 | 24.4** |
| Comparative Example 5 | " | 68.9 ± 6.6 | 21.4** |

**$p < 0.01$ relative to the untreated control group.

As is evident from the results shown in Table 1, the adhesive tapes according to the invention each gave a higher percent inhibition exceeding 30% as compared with the samples of the comparative examples for which the inhibition was about 16–25%.

TEST EXAMPLE 3

For investigating the effect of the antioxidant on the thermal degradation of the adhesive mass, each of the samples prepared in Examples 1 and 2 and Comparative Examples 3 and 4 as mentioned above was stored at 50° C. for a month and then subjected to the following tests:

(a) Tackiness testing by the rolling ball tack method (J. Dow's method)

The sample was placed on the slant of the testing apparatus at a gradient of 30° with the adhesive surface up. The upper and lower portions of the slant were covered with nonadhesive paper sheets from the respective slant ends, so that a 5-cm long adhesive surface portion was left in the middle of the slant. Steel balls differing in diameter were prepared and numbered 1, 2, 3, ... in the order of increasing diameter (the greater the diameter, the greater the number given).

Each ball was allowed to roll down the slant from the upper end thereof, and the number of the greatest ball prevented from rolling down on the adhesive surface portion in the middle of the slant was reported.

The results obtained in the above manner are shown in Table 2.

TABLE 2

| Sample | Initial | After 1-month storage at 50° C. |
|---|---|---|
| Example 1 | 38 | 40 |
| Example 2 | 40 | 40 |
| Comparative Example 3 | 40 | 32 |
| Comparative Example 4 | 40 | 30 |

As is evident from the results shown in Table 2, the samples prepared without addition of any antioxidant underwent decrease in cohesive strength, with the tendency that greater balls would not be stopped being increased.

(b) Tackiness testing by 180° peeling back from a Bakelite plate

Figure 2:
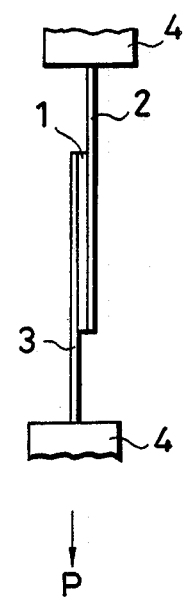
FIG. 2 shows, in partial side view, the tackiness test apparatus used in an example for illustrating the invention.

As shown in side view in FIG. 2, the sample 1, 25 mm in width and 100 mm in length, was provided at one end thereof with a lead paper 2 (fixed with an adhesive tape for fixation (not shown) and applied to the smooth surface of a Bakelite plate 3 (2 mm in thickness, 35 mm in width and 150 mm in length) as cleanly wiped with an acetone-impregnated cloth. The Bakelite plate with the sample was placed in a constant-temperature chamber maintained at 23±2° C., allowed to stand there for 1 hour and, then, mounted on a tensile tester. The tackiness was measured by pulling the sample in the direction of the arrow P at a speed of 300 mm/min. In FIG. 2, the numeral 4 indicates the chuck of the tester.

The results thus obtained are shown in Table 3.

TABLE 3

| Sample | Initial [g/25 mm] | After 1-month storage at 50° C. [g/25 mm] |
|---|---|---|
| Example 1 | 2120 ± 87 | 2250 ± 108 |
| Example 2 | 2200 ± 105 | 2010 ± 58 |
| Comparative Example 3 | 2430 ± 61 | 3570 ± 126 |
| Comparative Example 4 | 2380 ± 76 | 3810 ± 82 |

As is evident from the results shown in Table 3, the samples prepared in the comparative examples without using any antioxidant showed decreases in apparent cohesive strength and increases in tackiness as a result of oxidation during the 1-month storage at 50° C. On the contrary, the samples prepared in accordance with the invention showed little changes in tackiness after the long period of storage as compared with the initial values.

(c) Cohesive strength testing

A test piece (2.5 cm ×10 cm) was prepared from each sample, a terminal portion (2.5 cm ×2.5 cm) of the adhesive surface was made bare, and the test piece was applied to a Bakelite plate via the exposed adhesive surface portion. The Bakelite plate with the test piece was placed in an oven maintained at 50° C., with a load of 500 g applied to the other end of the test piece. The time required for the sample to drop off was measured. The results obtained are shown in Table 4.

TABLE 4

| Sample | Initial | After 1-month storage at 50° C. |
|---|---|---|
| Example 1 | >10 min | >10 min |
| Example 2 | >10 min | >10 min |
| Comparative Example 3 | >10 min | 320 seconds |
| Comparative Example 4 | >10 min | 580 seconds |

As is evident from the data shown in Table 4, the thermal stability of each of the samples prepared in accordance with the invention did not show any change even after the 1-month storage whereas decreases in cohesive strength and losses in thermal stability were observed with the samples prepared in the comparative examples.

What is claimed is:

1. An etofenamate-containing adhesive tape, which comprises a support member and an adhesive mass containing, as essential components thereof, about 1–20 wt.% of etofenamate, about 20–40 wt.% of a styrene-isoprene-styrene block copolymer, about 40–60 wt.% of a tackifier resin, about 0.1–20 wt.% of a liquid paraffin, about 5–20 wt.% of liquid polybutene rubber or liquid polyisoprene rubber and about 0.01–5 wt% of an antioxidant, and wherein said styrene-isoprene-styrene block copolymer has a styrene/rubber ratio of about 14/86, a hardness of about 38, and a 300% modulus of about 7 kg.

2. An etofenamate-containing adhesive tape as claimed in claim 1, wherein the tackifier resin is hydrogenated rosin or alicyclic saturated hydrocarbon petroleum resins.

3. The etofenamate-containing adhesive tape as claimed in claim 1, wherein the tackifier resin is hydrogenated rosin.

4. The etofenamate-containing adhesive tape as claimed in claim 1, wherein said antioxidant is dibutylhydroxytoluene or tetrakis(methylene-3,5-di-tert-butyl-4-hydroxyhydrocinnamate) methane.

5. The etofenamate-containing adhesive tape as claimed in claim 1, wherein said support member is made of a flexible material which is capable of changing shape in agreement with the motion of the human body.

6. The etofenamate-containing adhesive tape as claimed in claim 1, wherein said support member has perforations for releasing skin moisture.

7. The etofenamate-containing adhesive tape as claimed in claim 1, wherein said adhesive mass is spread over said support member at a coverage of about 50–500 g/cm$^2$.

* * * * *